US00PP09937P

United States Patent [19]

Zaiger et al.

[11] Patent Number: Plant 9,937

[45] Date of Patent: Jul. 1, 1997

[54] APRICOT TREE "EARLI-AUTUMN"

[76] Inventors: Chris Floyd Zaiger, 929 Grimes Ave.; Leith Marie Gardner, 1207 Grimes Ave.; Gary Neil Zaiger, 1907 Elm Ave.; Grant Gene Zaiger, 4005 California Ave., all of Modesto, Calif. 95358

[21] Appl. No.: 575,707

[22] Filed: Dec. 19, 1995

[51] Int. Cl.[6] ..... A01H 5/00

[52] U.S. Cl. ..... Plt./39

[58] Field of Search ..... Plt./39

*Primary Examiner*—James R. Feyrer

[57] ABSTRACT

A new and distinct variety of apricot tree *Prunus armeniaca*, which has the following unique combination of outstanding features that are desirable in a new variety:

1. Late maturity of fruit.
2. Producing mild, sweet, sub-acid fruit with good flavor and eating quality.
3. Fruit with good handling and shipping quality.
4. Heavy and regular production of fruit.
5. Vigorous, semi-spreading growth.
6. Fruit having a high soluble solids (average of 16.0 Brix).

1 Drawing Sheet

ORIGIN OF THE VARIETY

The present new and distinct variety of apricot tree was originated by us in our experimental orchard, located near Modesto, Calif., as a first generation cross between two selected seedlings, with field identification numbers 12H137 and 67EB393. The female parent, identification number 12H137, originated from a cross between Autumn Royal Apricot (U.S. Plant Pat. No. 2,906) and Tracy Apricot (U.S. Plant Pat. No. 3,062). The pollen parent, identification number 67EB393, originated from a cross between an open pollinated Modesto Apricot (U.S. Plant Pat. No. 2,543) seedling and a late maturing seedling of unknown parentage. A large group of these first generation seedlings were grown and maintained under careful observation by us and the present late maturing apricot variety evidenced the distinctive, desirable fruit characteristics described above and was selected for asexual reproduction and commercialization.

ASEXUAL REPRODUCTION OF THE VARIETY

The new and distinct variety of apricot tree was asexually reproduced by budding, as performed by us in our experimental located near Modesto, Calif., and shows that all characteristics run true to the original tree and are established and transmitted in succeeding propagations.

SUMMARY OF THE VARIETY

The new and distinct variety of apricot tree is of large size, vigorous, semi-spreading growth, and a heavy and regular bearer of yellow flesh, semi-freestone fruit with good flavor and eating quality. The fruit is further characterized by being medium in size, having good handling and shipping quality, having a high degree of soluble solids (average of 16.0 Brix), and ripening in the late maturity season.

BRIEF DESCRIPTION OF THE PHOTOGRAPH

The accompanying color photographic illustration shows typical specimens of the foliage and fruit of the present new variety of apricot tree. The upper and lower surface of the leaves are illustrated, the exterior and sectional view of the fruit being divided in the suture plane to reveal flesh coloration; pit cavity and a stone remaining in place. The photographic illustration was taken shortly after being picked at maturity (shipping ripe) and the colors are as nearly true as is reasonably possible in a color representation of this type.

DESCRIPTION OF THE VARIETY

The following is a detailed botanical description of the new and distinct variety of apricot tree, its flowers, foliage and fruit as based on observations of specimens grown near Modesto, Calif. with color terminology (except those in common terms) in accordance with Reinhold Color Atlas by A. Kornerup and J. H. Wanshcer.

Tree:
- *Size.*—Large.
- *Vigor.*—Vigorous.
- *Growth.*—Semi-spreading
- *Density.*—Medium dense.
- *Productivity.*—Productive.
- *Bearing.*—Regular.

Trunk:
- *Size.*—Large.
- *Texture.*—Shaggy.
- *Color.*—Brown to grayish brown (5-E-8) to (5--E-5).

Branches:
- *Size.*—Medium
- *Texture.*—Smooth to medium rough, varies with maturity.
- *Lenticels.*—Medium size. Numerous.
- *Color.*—New growth — greenish brown. Old growth — light brown to brown.

Leaves:
- *Size.*—Medium. Average length 4½". Average width 1¾".
- *Form.*—Ovate. Pointed.
- *Texture.*—Smooth.
- *Margin.*—Serrate.
- *Petiole.*—Average length 1⅛". Medium thickness.
- *Glands.*—Number varies from 1 to 4. Average number 3. Globose. Majority located on upper portion of petiole, few on base of leaf blade.
- *Color.*—Upper surface — green to dark green (29-F-6) to (29-F-7). Lower surface — light green to dull green (29-E-4) to (29-E-6).

Flower buds:
- *Size.*—Medium to large.
- *Length.*—Medium.
- *Form.*—Plump.

Flowers:
- *Blooming period.*—Date of first bloom: Mar. 1, 1994. Date of full bloom: Mar. 6, 1994. Varies slightly with climatic conditions.

*Size.*—Large.
*Color.*—Pink.
*Pollen.*—Present.

Fruit:
*Maturity when described.*—Firm ripe.
*Date of first picking.*—Aug. 8, 1994.
*Date of last picking.*—Aug. 12, 1994.
*Size.*—Medium. Average diameter axially 2⅛". Average diameter in suture plane 2⅛". Average diameter measured at right angles to suture plane 1".
*Form.*—Nearly Globose—sides slightly compressed toward suture plane and slightly flattened at base.
*Suture.*—Pronounced, extends from base to apex.
*Ventral surface.*—Nearly round, varies from round to very slightly lipped.
*Apex.*—Usually slightly retuse, varies from slightly retuse to round.
*Base.*—Retuse.
*Cavity.*—Slightly elongated in suture plane. Average depth ⅜". Average bredth ½".

Flesh:
*Ripens.*—Evenly.
*Texture.*—Firm.
*Amygdalin.*—Undetected.
*Juice.*—Moderate.
*Aroma.*—Moderate.
*Flavor.*—Good, mild, sweet, sub-acid.
*Eating quality.*—Good.
*Fibers.*—Very small, tender.
*Color.*—Yellow to light orange (4-A-5) to (5-A-3).

Skin:
*Thickness.*—Medium.
*Texture.*—Medium.
*Tendency to crack.*—None.
*Down.*—Moderate, short.
*Color.*—Light yellow to yellow (4-A-3) to (4-A-5).

Stone:
*Type.*—Semi-freestone. Amount of flesh adhering to stone varies slightly with fruit maturity.
*Size.*—Medium. Average length 1⅛". Average width ¾". Average thickness ½".
*Form.*—Oval to ovoid.
*Base.*—Usually straight—varies from straight to round.
*Apex.*—Usually slight point—varies from slight point to round.
*Sides.*—Equal to unequal.
*Ridges.*—Slight ridges extending across surface of the stone on opposite sides of suture plane.
*Surface.*—Slightly pitted throughout.
*Tendency to split.*—None.
*Color.*—Brown to dark brown 96-D-4) to (6-E-4).

Use: Dessert.
*Market.*—Local and long distance.
Keeping quality: Good.
Shipping quality: Good.

The present new variety of apricot tree, its flowers, foliage and fruit herein described many vary in slight detail due to cultural practices, soil types and climatic conditions under which the variety may be grown; the present description is that of the variety grown under the ecological conditions prevailing near Modesto, Calif.

We claim:

1. A new and distinct variety of apricot tree, substantially as illustrated and described, characterized by its large size, vigorous semi-spreading growth and a productive and regular bearer of medium size, yellow flesh, semi-freestone fruit with good flavor and eating quality; the fruit is further characterized by having good handling and shipping quality, having a high degree of soluble solids (average 16.0 Brix), and ripening in the late maturity season.

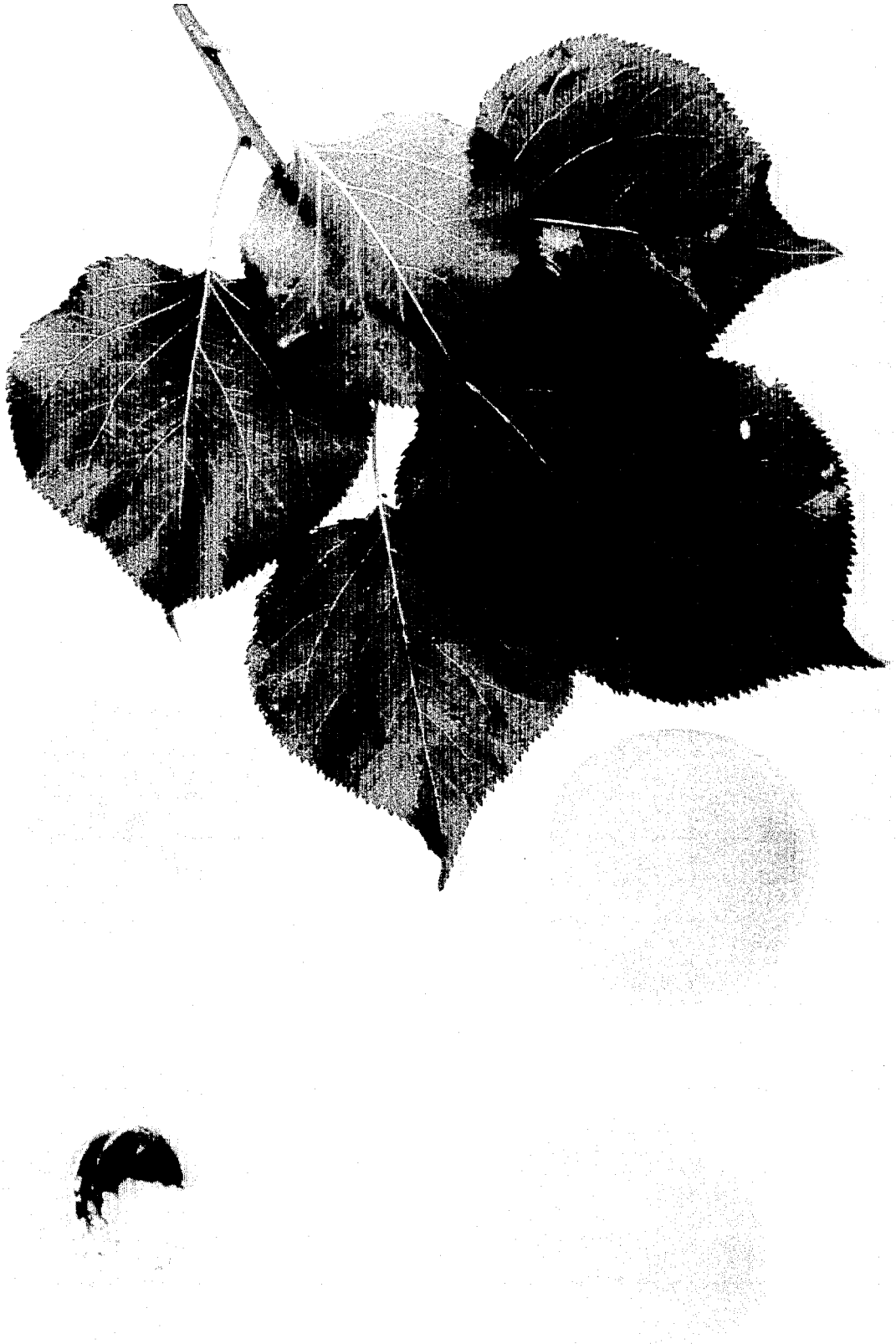

* * * * *